United States Patent
Andjelić

(10) Patent No.: US 7,652,127 B2
(45) Date of Patent: Jan. 26, 2010

(54) ABSORBABLE COPOLYESTERS OF POLY(ETHOXYETHYLENE DIGLYCOLATE) AND GLYCOLIDE

(75) Inventor: Saša Andjelić, Nanuet, NY (US)

(73) Assignee: Ethicon, Inc., Somerville, NJ (US)

( * ) Notice: Subject to any disclaimer, the term of this patent is extended or adjusted under 35 U.S.C. 154(b) by 170 days.

(21) Appl. No.: 11/554,675

(22) Filed: Oct. 31, 2006

(65) Prior Publication Data

US 2008/0103284 A1    May 1, 2008

(51) Int. Cl.
*C08G 63/02* (2006.01)
*C08G 64/00* (2006.01)

(52) U.S. Cl. .................. 528/272; 424/426; 528/300

(58) Field of Classification Search .............. 528/272, 528/300; 424/426
See application file for complete search history.

(56) References Cited

U.S. PATENT DOCUMENTS

| 4,048,256 | A |   | 9/1977  | Casey et al. |
| 4,080,969 | A |   | 3/1978  | Casey et al. |
| 4,095,600 | A |   | 6/1978  | Casey et al. |
| 4,122,129 | A |   | 10/1978 | Casey et al. |
| 5,644,002 | A |   | 7/1997  | Cooper et al. |
| 5,719,256 | A | * | 2/1998  | Tamai et al. ............. 528/361 |
| 2006/0051398 | A1 |  | 3/2006  | Andjelic et al. |

FOREIGN PATENT DOCUMENTS

WO    WO 2006/125098 A    11/2006

OTHER PUBLICATIONS

International Search Report dated May 9, 2008 for International Appln. No. PCT/US2007/082773.

* cited by examiner

*Primary Examiner*—Terressa M Boykin
(74) *Attorney, Agent, or Firm*—Roberts Mlotkowski Safran & Cole, P.C.

(57) ABSTRACT

A semi-crystalline, absorbable copolyester composition comprising the reaction product of a polycondensation polyester and at least one lactone, wherein the polycondensation polyester comprises the reaction product of diglycolic acid and/or a derivative thereof and diethylene glycol; and the copolyester comprises about 30 to 50% by weight of the polycondensation polyester based on the total weight of the copolyester.

11 Claims, No Drawings

ABSORBABLE COPOLYESTERS OF POLY(ETHOXYETHYLENE DIGLYCOLATE) AND GLYCOLIDE

FIELD OF THE INVENTION

The present invention relates to a composition comprising a semi-crystalline, absorbable copolyester comprising the reaction product of a polycondensation polyester and at least one lactone, more specifically, a semi-crystalline absorbable copolyester comprising the reaction product of poly(ethoxyethylene diglycolate) and glycolide, where the copolyester comprises about 30 to 50% by weight of the poly(ethoxyethylene diglycolate) based on the total weight of the copolyester.

BACKGROUND OF THE INVENTION

Mechanical properties of a medical device can be made to vary depending on the end use application for the device. For example, it is often desirable for surgical sutures to exhibit mechanical strength, such as straight tensile strength and knot tensile strength. One technique for producing surgical sutures having these desired properties is to utilize polymers having some degree of crystallinity. Specifically, the crystalline or ordered structure of the polymer imparts strength to a medical device produced therefrom, including but not limited to a surgical suture, surgical mesh, surgical staple, hemostatic clip, and the like.

In general, however, the greater the crystallinity of an absorbable polymer, the slower the rate of the absorption will be. Therefore, in those applications where an absorbable medical device is desired, there is a need to balance the level of crystallinity of the polymer against the absorbability thereof. For example, there are certain applications where there is a need for an absorbable medical device to absorb quickly, such as episiotomy and plastic surgical applications, where fast absorption of the medical device is highly desirable to improve patient comfort and to achieve aesthetic outcomes, respectively.

Several approaches to increase the absorption or hydrolysis rate of absorbable polymers are known. For example, one approach is to lower the crystallinity of the polymer to enhance the absorption or hydrolysis rate thereof. This may be done by randomizing the chemical structure of the polymer using, for example, different lactones in the copolymerization step to reduce the overall crystallinity of the polymer. However, the use of lactones to disrupt crystallinity has limited impact due to the considerably higher hydrophobicity of lactone, causing the resultant polymer and medical device to be more hydrophobic, and absorption or hydrolysis to occur more slowly. In addition, lowering the level of crystallinity of the polymer may adversely affect the physical properties of the medical device prepared therefrom.

A second approach to increase the absorption or hydrolysis rate of synthetic absorbable polymers is to add a non-absorbable hydrophilic moiety, e.g. a polyether such as polyethylene glycol (PEG), to increase the hydrophilicity of absorbable polymer. However, such approach will result in poor mechanical properties of the medical device (e.g. tensile strength and modules) due to the general chemical structure of aliphatic polyethers, and the addition of PEG moieties will reduce the overall crystallinity of the polymers.

A third approach is to use a pre-degraded synthetic absorbable polymer. For example, an absorbable polymer may be subjected to a hydration step or gamma irradiated to initiate the hydrolysis of the absorbable polymer, thereby resulting in a pre-degraded product. However, problems arising with the use of a pre-degraded synthetic absorbable polymer include difficulty in controlling the quality and stability of the pre-degraded polymer. More specifically, it may be difficult to achieve reproducible levels of pre-degradation in the final product.

U.S. Patent Publication 2006/0051398, assigned to Ethicon, Inc., describes a copolyester comprising the reaction product of a polycondensation polyester and at least one lactone, wherein the polycondensation polyester comprises the reaction product of diglycolic acid and/or a derivative thereof and ethylene glycol. The product described in this reference is useful for adhesion prevention. Although this reference indicates that its composition is absorbable, the copolyester described in this reference is fully amorphous with relatively low molecular weight. Therefore, it is not expected that a medical device made from this copolyester will have the requisite physical properties of strength required, for example, for surgical sutures.

U.S. Pat. No. 5,644,002, also assigned to Ethicon, Inc., describes absorbable polymers and blends of polycondensation polyester and aliphatic polyesters based on lactone monomers, where the polycondensation polyester is the reaction product of diglycolic acid and an alcohol selected from selected from the group consisting of glycerol, pentaerythitol, trimethylolpropane, hydroxyl terminated poly(ethylene glycol)s, ethylene glycol, 1,2-propanediol, 1,3-propanediol, 1,4-butylene glycol, dipropylene glycol, 1,5-pentanediol, 1,6-hexanediol, 1,7-heptanediol, and 1,8-octanediol. The absorbable polymers described in this reference are branched or crosslinked fully amorphous soft materials and as such, are not expected to produce a medical device having the requisite physical properties of strength required, for example, for surgical sutures.

U.S. Pat. Nos. 4,048,256, 4,095,600 and 4,122,129, assigned to American Cyanamid Company, describe biocompatible and absorbable polycondensation polyesters, which are the polycondensation product of diglycolic acid and glycols such as ethylene glycol, diethylene glycol, 1,2-propylene glycol, 1,3-propylene glycol, and the like. Specifically, U.S. Pat. No. 4,095,600 describes a transesterification reaction product of (a) about 2 to 50% by weight of a polycondensation polyester made of diglycolic acid and an unhindered glycol and (b) polyglycolic acid (PGA) of molecular weight above 30,000 Daltons before reaction. Although it is believed that the transesterification reaction product described in this reference exhibits crystallinity, the absorbability thereof is not expected to be very good due to the high melting point of the PGA moieties.

Therefore, there remains a need for a synthetic absorbable polymer that will achieve faster absorption or hydrolysis, while preserving mechanical strength that is required, for example, for surgical sutures.

SUMMARY OF THE INVENTION

Described herein is a composition comprising a semi-crystalline, absorbable copolyester comprising the reaction product of a polycondensation polyester and at least one lactone, wherein the polycondensation polyester comprises the reaction product of diglycolic acid and/or a derivative thereof and diethylene glycol; and the copolyester comprises about 30 to 50% by weight of the polycondensation polyester based on the total weight of the copolyester.

DETAILED DESCRIPTION

The present invention relates to a composition comprising a semi-crystalline, absorbable copolyester of a polycondensation polyester and at least one lactone, more specifically, a semi-crystalline absorbable copolyester comprising the reaction product of poly(ethoxyethylene diglycolate) (PEEDG) and at least one lactone, where the copolyester comprises about 30 to 50% by weight of the poly(ethoxyethylene diglycolate) based on the total weight of the copolyester.

In one embodiment of the present invention, the copolyester comprises the reaction product of a polycondensation polymer and at least one lactone, wherein the polycondensation polyester comprises the reaction product of diglycolic acid and/or a derivative thereof and diethylene glycol.

In another embodiment, the polycondensation polyester comprises the reaction product of diglycolic acid and/or a derivative thereof, up to about 25 mole percent of an aliphatic diacid based on the total moles of acid, and diethylene glycol. Specifically, the aliphatic diacid may be an aliphatic alpha-omega dicarboxylic acid, including but not limited to 3,6-dioxaoctanedioic acid, 3,6,9-trioxaundecanedioic acid, and combinations thereof.

The polycondensation polyester may be synthesized by conventional techniques. For example, in a condensation polymerization, diglycolic acid and diethylene glycol may be polymerized in the presence of a catalyst at elevated temperatures and reduced pressures. A variety of catalysts may be used, but organometallic compounds have been found to be useful. The catalyst for the polycondensation step of the synthesis is preferably tin based, e.g., stannous octoate. The most desirable catalyst is dibutyltin oxide and is present in the diglycolic acid/diethylene glycol monomer mixture at a sufficiently effective molar ratio of monomer to catalyst, e.g., ranging from about 5,000/1 to about 100,000/1. For example, the ratio of 10,000/1 has been found to be quite suitable. The reaction is typically carried out at a temperature range from about 100° C. to about 220° C., preferably from about 140° C. to about 180° C., under an inert atmosphere until esterification of diglycolic acid is complete. Preferably, 165° C. has been found to be a desirable reaction temperature when employing a vertically stirred reactor. It should be noted that the optimum reaction temperature may be reactor and catalyst level dependent but can be found by one having only ordinary skill through the use of experiments. The first stage of the polycondensation reaction (inert gas at atmospheric pressure) is followed by polymerization under reduced pressure until the desired molecular weight and viscosity are achieved.

The weight average molecular weight of the polycondensation polymer can range from about 20,000 to about 50,000 g/mol, preferably from about 30,000 to about 50,000 g/mol, most preferably about 40,000 g/mol. This corresponds to an inherent viscosity range from about 0.68 to about 1.0 dL/g. When the molecular weight of the polycondensation polymer is lower than about 20,000 g/mol, the molecular weight of the final copolyester is too low to achieve the desired mechanical properties, for example, for suture applications. Although molecular weight can be increased with increasing reaction time, it becomes increasingly difficult to achieve very high molecular weight. We have found, in general, that a molecular weight of the polycondensation polymer greater than about 50,000 g/mol, is not necessary to achieve desirable properties. One could however envision that this value is not an absolute bar. One might for instance, increase the molecular weight of the polycondensation polymer, and lower the amount of the lactone monomer used in the preparation of the final copolyester.

PEEDG is a fully amorphous polycondensation product of diglycolic acid and diethylene glycol. When the diethylene glycol is used in excess, the resultant polycondensation product contains hydroxyl-capped end groups, and is then capable of serving as a macroinitiator in the subsequent, second stage ring-opening polymerization with a lactone monomer, such as glycolide. When PEEDG is reacted with lactone monomers such as glycolide and transesterification reactions are minimized, block glycolide sequences form and the resultant copolyester is a crystallizable material. More specifically, this results in a semi-crystalline copolyester, which are properties that are particularly advantageous, for example, in fiber manufacturing processes. Additionally, the crystallization rate of the copolyester is observed to be fast, which is another advantageous property, for example, in fiber manufacturing processes. Finally, both the PEEDG and the copolyester product derived therefrom are hydrophilic and fast-absorbing polymers.

The amount of polycondensation polyester used to prepare the copolyester of the present invention ranges from about 30 to 50% by weight based on the total weight of the copolyester.

Suitable lactone monomers that may be reacted with the polycondensation polyester include, but are not limited to, glycolide, lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations of two or more thereof. The preferred lactone monomer includes glycolide.

In one embodiment, the copolyester may comprise the reaction product of a polycondensation polyester such as poly(ethoxyethylene diglycolate) and a lactone such as glycolide.

In another embodiment, the copolyester may comprise the reaction product of a polycondensation polyester and two or more lactones. For example, the copolyester may comprise the reaction product of the polycondensation polyester, at least 75 mole percent glycolide based on the total moles of lactone, and a second lactone monomer.

The copolyesters of the present invention may be conveniently synthesized by reaction of a dihydroxy poly(alkylene diglycolate) homopolymer or copolymer with a lactone by conventional techniques using conventional processes. For example, the polycondensation polyester is used as an α,ω-dihydroxy macroinitiator in a subsequent ring opening polymerization (ROP) with a lactone or a lactone mixture. The lactone monomers are copolymerized into the polycondensation polyester in the presence of a conventional organometallic catalyst at elevated temperatures. The catalyst for the ROP may be already present as residual catalyst in the polycondensation polyester or may be additional catalyst added in this second step of the synthesis. A suitable catalyst added at the time of the ROP can be an organometallic catalyst. The ring-opening organometallic catalyst is preferably tin based, e.g., stannous octoate, and is present in a sufficiently effective amount in the monomer mixture, preferably at a molar ratio of lactone monomer-to-catalyst ranging from about 20,000/1 to infinity (i.e. no additional catalyst used). Thus one might utilize a tin-IV compound such as dibutyltin oxide at a diacid, for instance, diglycolic acid-to-catalyst ratio of about 10,000/1 to prepare the polycondensation polyester and then add a tin-II compound such as stannous octoate at a lactone-to-added-catalyst molar ratio of about 240,000/1 at the time of the ring opening polymerization. The copolyesters of the present invention may be synthesized alternately with no additional catalyst being added at the time of the ROP as described in Example 2.

The ROP step can be immediately conducted in the same reactor as that used to synthesize the polycondensation polyester immediately after the completion of the polycondensation step, if the reactor can provide adequate heat transfer and agitation. The lactone or lactone mixture can be added as a solid, a slurry, or in molten form. Alternately, the ROP can be conducted in a separate reactor at a later date, or in the reactor used for the polycondensation polyester at a later date. If this is the case, the polycondensation polyester is discharged from its reactor and is stored in an environment that minimizes water pick up and hydrolysis. In the case of adding glycolide monomer, the monomer can be added as a solid. The reactor is closed and the pressure reduced. The reactor is usually held under vacuum for a prolonged period of time, for instance overnight, to allow drying. Nitrogen is then introduced into the reactor to bring the pressure to slightly greater than one atmosphere, and the purge cycle repeated for a total of three times. The temperature of the reaction mass is brought up to 130° C. Once at this temperature, the agitator is activated. The temperature is then increased to 150° C. to complete the mixing. This mixing step is essential to produce the copolyesters of the present invention as inadequate mixing tends to allow the formation of homopolymeric sequences which can then crystallize to an extent greater than optimum. To ensure that reactants are fully mixed, in-situ spectroscopic probes (such as Near-Infrared) can be conveniently used. If additional catalyst is to be added, it is typically added once the batch has been completely mixed. The temperature is quickly brought up to the final reaction temperature, with 210° C. being a most preferred temperature, and held there for typically 2 hours. The exact reaction conditions will depend on the catalyst and its level; final reaction temperatures can vary from about 195° C. to 235° C., and more preferably from about 200° C. to about 220° C. Reaction times can vary from about 30 minutes to a few hours, depending on the catalyst and it level, and is typically conducted until the desired conversion of monomer to polymer is achieved.

An alternate reaction scheme that has been employed to prepare the copolyesters of the invention has involved adding the lactone as a molten stream into the reactor. Thus the polycondensation polyester is added first, typically as a molten stream and the reactor evacuated. The reactor is heated to 130° C. Molten glycolide (or other glycolide rich mixture) at a temperature of 100° C. is added to the reactor. Although the batch temperature drops slightly, it is quickly brought back up to 130° C. at which point mixing is started. At this point, the process that was described above is followed.

Under the above described conditions, the copolyesters of polycondensation polyester and lactones, will typically have a weight average molecular weight of about 40,000 g/mol (a.k.a. Daltons) to about 100,000 g/mol, preferably about 50,000 g/mol to about 80,000 g/mol, and more preferably about 60,000 g/mol to about 80,000 g/mol,. These molecular weights are sufficient to provide an effective inherent viscosity, typically between about 1.0 to about 2.5 deciliters per gram (dL/g), preferably about 1.2 to about 2.0 dL/g, more preferably about 1.4 to about 1.8 dL/g, as measured in a 0.1 g/dL solution of hexafluoroisopropanol (HFIP) at 25° C.

The crystallinity of the copolyester described herein ranges from about 20 to about 40% crystallinity, and preferably from about 20 to about 30%. It has been discovered that the use of diethylene glycol to prepare the polycondensation product, PEEDG, instead of ethylene glycol as described in U.S. Patent Publication 2006/0051398, results in a copolyester product that is semi-crystalline, instead of an amorphous product.

The copolyester having the weight average molecular weights described herein may be extruded into fibers or sutures for use in a surgical wound site or trauma site, or used to make other medical devices such as meshes. Alternatively, articles may be molded from the copolyester described herein by various conventional injection and extrusion molding processes. For example, the copolyester may be molded to form, without limitation, sutures, meshes, films, orthopedic devices and injection molded devices. Alternatively, the copolyester may be a component of a medical device, i.e., the copolyester may form one layer of a multi-laminate hernia repair mesh, or may be suspended in a polymer solution and coated onto at least a portion of a medical device.

EXAMPLE 1

Synthesis of Synthesis of Hydroxy Terminated Poly(ethoxyethylene diglycolate) (PEEDG)

A dual-agitated reactor with intermeshing HELICONE patterned blades (D.I.T. 10CV reactor) was employed. After charging the reactor with 7.0 kg of diglycolic acid, 16.6 kg of diethylene glycol (DEG) and 1.3 grams of dibutyltin oxide catalyst, the pressure was reduced to below 1 Torr and the vacuum preserved over night. The next day vacuum was released by introducing dry nitrogen (argon can be substituted) and heating of the mixture was started, and the agitator was stared and set to 15 RPM in reverse. When the reactor temperature reached 150° C., the agitator speed was reset to 20 RPM in forward direction. Soon first distillate appeared containing mostly water, an esterification by-product. The reaction was continued at 170° C. for about 2 hours until approximately all water was distilled and/or first traces of EG appeared in the distillate. After the first nitrogen/argon stage was completed, pressure was lowered gradually to full vacuum while the temperature of the batch was maintained at 170° C. A vacuum of about 30-50 mTorr was maintained throughout the rest of the reaction, a total time of approximately 80 hours. Melt and solution viscosities were regularly checked to ensure polycondensation polyester of a desired molecular weight. Hydroxy end-capped polycondensation polyester was discharged after approximately 66 (sample 1A) and 80 hours (1B) of reaction time under vacuum. Both portions were a fully amorphous, colorless viscous liquid with a glass transition temperature of about −13.0 and −11.5° C., respectively. Weight average molecular weight was about 21,000 and 27,000 g/mol respectively; the resin sample V+66 hours exhibited an inherent viscosity (IV) of 0.69 dL/g, while the sample discharged at V+80 hours had IV of 0.84 dL/g, as determined in HFIP at 25° C. at a concentration of 0.1 g/dL.

EXAMPLE 2

Synthesis of Copolyester I: The Copolymerization of an α,ω-Dihydroxy Poly(ethoxyethylene diglycolate) Homopolymer with a Lactone Monomer, Glycolide, (PEEDG/Gly 40/60)

A portion of the polycondensation polyester (7.4 kg) produced as described in Example 1 (V+80, sample portion "B") was held in the DIT 10CV reactor at room temperature under nitrogen. A S/S melt-tank was used to melt the crystalline glycolide, prior to the addition into the reactor with the polycondensation polyester to be added later in a liquid state. The glycolide (11.1 kg) was charged to the melt-tank, pulled under vacuum, and then heated and held under nitrogen at 120° C. After the polycondensation polyester was heated to approximately 120° C., at which point the molten glycolide monomer was transferred from the melt tank with agitation. Agitator mixing was continued (20 RPM) and the batch temperature raised to 225° C. for a short period, to assure that there was no PGA "freeze-up". In situ, a real-time Fourier Transform Near-Infrared probe was used to confirm complete mixing of components. The temperature was then reduced to 210° C. and the reaction was continued for another two hours. The discharged co-polyester was slightly crystalline, with a brownish to slightly yellow tint, and had a glass transition temperature of 14.5° C. Weight average molecular weight was approximately 60,000 g/mol and an inherent viscosity of 1.38 dL/g, as determined in HFIP at 25° C. at a concentration of 0.1 g/dL, was recorded. The composition was confirmed by $H^1$ NMR to be 40/60 by weight poly(ethoxyethylene diglycolate-co-glycolide). The copolymer was sized to approximately 3/16" granules in a rotating knife granulator, sieved to remove fines, and placed in a Patterson-Kelley twin-shell tumble dryer. The resin was subjected to full vacuum at ambient temperature for approx. 18 hours, at which point heat was introduced to the dryer. The dryer was heated to 110° C. for apprx. 24 hours with full vacuum (<200 mtorr) at which point the heat was removed, and the vessel allowed to cool to room temperature. The resin was removed from the dryer, placed in vacuum containers and held under vacuum until further use.

The combined sources of tin in Example 2 result in a lactone-to-total-tin-catalyst ratio of about 28,300/1 the total tin in the final copolyester is about 32 ppm on a weight basis.

EXAMPLE 3

Synthesis of Copolyester II: The Copolymerization of an α,ω-Dihydroxy Poly(ethoxyethylene diglycolate) Homopolymer with a Glycolide, (PEEDG/Gly 30/70)

A portion of the polycondensation polyester produced as described in Example 1 (1.8 kg) having weight average molecular weight of 21,000 g/mol and inherent viscosity of 0.69 dL/g (V+66 h, sample portion "A"), was reacted with glycolide monomer (4.2 kg) by ring-opening polymerization according to procedures described in Example 2. Final composition revealed by NMR was PEEDG/Gly 30/70 wt. %. This copolymer is semi-crystalline, with the weight average molecular weight of 42,000 g/mol and inherent viscosity of 1.18 dL/g.

EXAMPLE 4

Synthesis of Copolyester III (PEEDG/Gly 40/60)

A portion of the polycondensation polyester produced as described in Example 1 (6.1 kg) having weight average molecular weight of 12,700 g/mol and inherent viscosity of 0.35 dL/g, was reacted with glycolide monomer (9.1 kg) by ring-opening polymerization according to procedures described in Example 2. The final composition revealed by NMR was PEEDG/Gly 40/60 wt. %. This copolymer is semi-crystalline, with the weight average molecular weight of 24,000 g/mol and inherent viscosity of 0.80 dL/g.

EXAMPLE 5

Synthesis of Copolyester IV (PEEDG/Gly 30/70)

A portion of the polycondensation polyester produced as described in Example 1 (4.1 kg) having weight average molecular weight of 12,700 g/mol and inherent viscosity of 0.35 dL/g, was reacted with glycolide monomer (9.5 kg) by ring-opening polymerization according to procedures described in Example 2. The final composition revealed by NMR was PEEDG/Gly 30/70 wt. %. This copolymer is semi-crystalline, with the weight average molecular weight of 24,000 g/mol and inherent viscosity of 0.79 dL/g.

EXAMPLE 6

Melt index testings were conducted on several PEEDG/Gly copolymers to determine their melt properties suitable for fiber extrusions. Melt index testings are performed on Melt Index Plastometer (manufactured by Tinius & Olsen, Willow Grove, Pa., USA). The procedure is described as follows. The material to be tested is inserted into the bore of a preheated Plastometer (e.g. 195-235° C.) containing the designated die. A piston rod containing a known weight (e.g. 3,700 g) is placed on the top of the polymer. The weight forces the melted polymer to flow through a die of predetermined length and diameter at the preset temperature (e.g. 195-235° C.), which is above the melting point of the polymer. Next, the portions of extruded polymers, obtained at designated time intervals, are accurately weighed to determine a weight per unit of time measurements. Melt index (MI) is generally defined as grams of polymers that are collected through the die for the time of 10 minutes. Using this method, accurate comparisons can be made to evaluate the flow characteristics of similar or different polymers at constant conditions.

TABLE 1

Melt index test of different PEEDG/Gly copolymers.

| Copolyester ID | Composition | Mw (g/mol) | Tm (° C.) | Condition | Melt index, MI (g/10 min) |
|---|---|---|---|---|---|
| Copolyester I | PEEDG/Gly 40/60 | 60,000 | 192 | T = 235° C., w = 3,700 g | 1.039 |
|  |  |  |  | T = 200° C., w = 3,700 g | 0.372 |
| Copolyester II | PEEDG/Gly 30/70 | 42,000 | 205 | T = 235° C., w = 3,700 g | Failed |
|  |  |  |  | T = 210° C., w = 3,700 g | 1.075 |
|  |  |  |  | T = 210° C., w = 3,700 g | No flow |
| Copolyester III | PEEDG/Gly 40/60 | 24,000 | 188 | T = 225° C., w = 3,700 g | Failed |
|  |  |  |  | T = 195° C., w = 3,700 g | Failed |
| Copolyester IV | PEEDG/Gly 30/70 | 24,000 | 195 | T = 200° C., w = 3,700 g | Failed |

"Failed" MI samples indicate that melt viscosity is too low for these materials to be measured. This indirectly implies that these copolyesters cannot be extruded into fibers. Data for copolyester II indicate that only extrusion at low temperature melt conditions (slightly above its melting point) may have suitable melt viscosity.

EXAMPLE 7

Crystallization properties of several PEEDG/Gly copolyesters were determined using differential scanning calorimetry (DSC). Overall crystallization rates depend principally on two factors: the concentration of growing spherulites over time (nucleation rate) and the rate of spherulitic growth. As expected, these processes have a measurable effect on calorimetric data. Calorimetric results were generated on a TA Instruments Differential Scanning Calorimeter, Model 2910 MDSC, using dry $N_2$ as a purge gas. Crystallization studies were conducted in the following manner: after melting, the sample was subjected to the cooling step from the melt at a constant cooling rate of 10° C./min. Crystallization is manifested by the endothermic peak, whose high temperature slope is used to determine crystallization rate, while the area under the peak (heat of crystallization, $\Delta H_c$) is associated with the overall level of crystallinity.

TABLE 2

Crystallization properties of PEEDG/Gly copolyesters

| Copolyester ID | Composition | IV (dL/g) | $T_{cryst}$ (° C.) | $\Delta H_c$ (J/g) | Cryst. Rate (W/g/° C.) |
|---|---|---|---|---|---|
| Copolyester I | PEEDG/Gly 40/60 | 1.38 | 137.0 | 39.5 | −0.0342 |
| Copolyester II | PEEDG/Gly 30/70 | 1.18 | 145.5 | 41.0 | −0.0370 |
| Copolyester III | PEEDG/Gly 40/60 | 0.80 | 119.5 | 42.5 | −0.0166 |
| Copolyester IV | PEEDG/Gly 30/70 | 0.79 | 101.5* | 12.5 | −0.0018 |

*another smaller crystallization peak observed at 205° C.

Fast crystallization kinetics of copolyesters I and II suggest that these materials may be easy to extrude into fibers. If the copolyester crystallizes too slowly it cannot be extruded into fibers, such as the case for copolyesters III and IV. Therefore, for the copolyester to be extruded into fibers two major conditions need to be met. First, the copolyesters must have a suitable melt viscosity (MI), and second, the copolyesters must have relatively fast crystallization kinetics.

EXAMPLE 8

A monofilament 2/0 (d=14 mil) was made from Copolyester I as described above using cold drawing procedure under following processing conditions:

Die temperature: 200° C.
Water bath temperature: 20° C.
Speed of the first set of Godets (not heated): 15 RPM
Speed of the second set of Godets (not heated): 100 RPM
Speed of the third set of Godets (not heated): 110 RPM
Overall draw ratio for Fiber-C was 7.2
First oven temperature: 80° C.
Second oven temperature: 95° C.
Monofilaments appear to be smooth, elastic but yet strong.

Thermal properties of the fiber are determined using differential scanning calorimetry, and are listed in Table 3.

TABLE 3

Thermal and crystallization properties of the neat resin and of the selected experimental monofilaments

| Polymer | Fiber Tensile Strength (lbs) | Tm (° C.) | $\Delta H_m$ (g/mol) | Tc* (° C.) | $\Delta H_c$* (g/mol) | Cryst. Rate* (W/g/° C.) |
|---|---|---|---|---|---|---|
| Neat resin | / | 196.0 | 24.0 | 137.0 | 39.5 | −0.034 |
| Fiber-C | 13 | 193.5 | 22.0 | 132.0 | 37.5 | −0.031 |

*data obtained from the cooling from the melt with the constant cooling rate of 10° C./min DSC data indicate that the polymer extruded under the conditions described above did not randomize appreciably compared to the original polymer (neat resin), and did not loose ability to crystallize fast (compared to the neat resin), as indicated from crystallization rate in Table 3.

EXAMPLE 9

Tensile properties were determined using Instron testing machine on the unannealed monofilament. Sample rate was 20 pts/secs with crosshead speed of 12 in/min; full scale load range=100 lbf. In Table 4, selected tensile properties (mean values) are given for Fiber-C sample and for the same fiber with a single knot made in the middle of the thread;

TABLE 4

Selected Tensile properties of unannealed Fiber-C

| Sample | Diameter (mil) | Load at the break (lbs) | Stress at max load (kpsi) | Elongation (%) | Young's Modulus (kpsi) |
|---|---|---|---|---|---|
| Fiber-C | 14.4 | 12.8 | 78.2 | 29.6 | 347 |
| Fiber-C with a knot | 14.4 | 9.3 | 57.2 | 24.5 | 300 |

As Table 4 indicates, excellent mechanical properties are observed for unannealed Fiber-C sample. More significantly, substantial knot security was maintained (73% of the strength) for Fiber-C as indicated in the Table 4.

Although this invention has been shown and described with respect to detailed embodiments thereof, it will understood by those skilled in the art that various changes in form and detail thereof may be made without departing from the spirit and scope of the claimed invention.

What is claimed is:

1. A composition comprising an absorbable copolyester comprising the reaction product of a polycondensation polyester and at least one lactone monomer,
    wherein the polycondensation polyester comprises the reaction product of diglycolic acid and diethylene glycol;
    the copolyester comprises about 30 to 50% by weight of the polycondensation polyester based on the total weight of the copolyester; and
    the copolyester has a crystallinity ranging from about 20 to 40%.

2. The composition according to claim 1, wherein the at least one lactone monomer is glycolide.

3. The composition according to claim 1, wherein the copolyester comprises the reaction product of a polycondensation polyester, at least 75 mole percent glycolide based on the total moles of lactone, and a lactone selected from the group consisting of lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2,-one, 1,4-dioxan-2-one, 6,8-dioxabicycloctane-7-one, and combinations thereof.

4. The composition according to claim 1, wherein the polycondensation polyester comprises the reaction product of diglycolic acid, up to about 25 mole percent of an aliphatic diacid based on the total moles of acid, and diethylene glycol.

5. The composition according to claim 1, wherein the weight average molecular weight of the copolyester is from about 40,000 to about 100,000 g/mol.

6. The composition according to claim 1, wherein weight average molecular weight of the copolyester is from about 50,000 to about 80,000 g/mol.

7. The composition according to claim 1, wherein weight average molecular weight of the copolyester is about 60,000 to about 80,000 g/mol.

8. The composition according to claim 1, wherein weight average molecular weight of the polycondensation polymer is from about 20,000 to about 50,000 g/mol.

9. The composition according to claim 1, wherein weight average molecular weight of the polycondensation polymer is from about 30,000 to about 50,000 g/mol.

10. The composition according to claim 1, wherein weight average molecular weight of the polycondensation polymer is about 40,000 g/mol.

11. A surgical suture or mesh comprising an absorbable copolyester that is the reaction product of a polycondensation polyester and at least one lactone monomer,
   wherein the polycondensation polyester comprises the reaction product of diglycolic acid and diethylene glycol;
   the copolyester comprises about 30 to 50% by weight of the polycondensation polyester based on the total weight of the copolyester; the copolyester has a crystallinity ranging from about 20 to 40%; and
   the weight average molecular weight of the copolyester ranges from about 40,000 to about 100,000 g/mol.

* * * * *